(12) United States Patent
Lawson et al.

(10) Patent No.: US 7,790,414 B2
(45) Date of Patent: Sep. 7, 2010

(54) METHODS FOR PRODUCING ANTIBODIES

(75) Inventors: Alastair David Griffiths Lawson, Hampshire (GB); Daniel John Lightwood, Slough (GB)

(73) Assignee: UCB Pharma S.A., Brussels (BE)

( * ) Notice: Subject to any disclaimer, the term of this patent is extended or adjusted under 35 U.S.C. 154(b) by 533 days.

(21) Appl. No.: 10/558,572

(22) PCT Filed: May 24, 2004

(86) PCT No.: PCT/GB2004/002226

§ 371 (c)(1),
(2), (4) Date: Jan. 24, 2006

(87) PCT Pub. No.: WO2004/106377

PCT Pub. Date: Dec. 9, 2004

(65) Prior Publication Data

US 2007/0009959 A1 Jan. 11, 2007

(30) Foreign Application Priority Data

May 30, 2003 (GB) ................................. 0312481.5

(51) Int. Cl.
*C12P 21/08* (2006.01)
*G01N 33/577* (2006.01)
(52) U.S. Cl. ...................... 435/69.6; 435/70.4; 436/548
(58) Field of Classification Search ........................ None
See application file for complete search history.

(56) References Cited

U.S. PATENT DOCUMENTS

| 4,816,397 | A | 3/1989 | Boss et al. ..................... 435/68 |
| 5,585,089 | A | 12/1996 | Queen et al. ............. 424/133.1 |
| 6,331,415 | B1 | 12/2001 | Cabilly et al. .............. 435/69.6 |
| 2005/0147609 | A1* | 7/2005 | Filvaroff ................... 424/145.1 |

FOREIGN PATENT DOCUMENTS

| EP | 0488470 A1 * | 6/1992 |
| EP | 0 488 470 B1 | 5/1997 |
| WO | 91/09967 A1 | 7/1991 |
| WO | 92/02551 A1 | 2/1992 |
| WO | 01/55216 A1 | 8/2001 |
| WO | 2003/093320 A3 | 11/2003 |

OTHER PUBLICATIONS

Rudikoff et al, Proc. Natl. Acad. Sci. USA (1982) vol. 79, pp. 1979-1983.*
Rader et al, Proc. Natl. Acad. Sci. USA (1998) vol. 95, 8910-8915.*
Simonsson, A.C., et al., "Single, antigen-specific B cells used to generate Fab fragments using CD40-mediated amplification or direct PCR cloning," BioTechniques, 1995, 18(5), 862-869.*
Hood et al, Immunology, Second Edition, Benjamin/Cummings Publishing Company, Inc., 1984, pp. 58-60.*

Babcook, J.S., et al., "A novel strategy for generating monoclonal antibodies from single, isolated lymphocytes producing antibodies of defined specificities," *Proc. Natl. Acad. Sci. USA*, 1996, 93, 7843-7848.
Bird, R.E., et al., "Single-chain antigen-binding proteins," *Science*, 1988, 242, 423-426.
Boder, E.T., et al., "Directed evolution of antibody fragments with monovalent femtomolar antigen-binding affinity," *Proceedings of the National Academy of Science*, 2000, 97(20), 10701-10705.
Chang, T.W., et al., "In-vitro response to hepatitis B surface antigen of peripheral blood lymphocytes from recipients of hepatitis B vaccine," *Hepatology*, 1984, 4(5), 824-829.
de Wildt, R.M.T., et al., "A new method for the analysis and production of monoclonal antibody fragments originating from single human B cells," *J. of Immunological Methods*, 1997, 207, 61-67.
Jerne, N.K., et al., "Plaque formation in Agar by single antibody-producing cells," *Science*, 1963, 140, p. 405.
Karlsson, R., et al., "Kinetic analysis of monoclonal antibody-antigen interactions with a new biosensor based analytical system," *J. Immunol. Methods*, 1991, 145, 229-240.
Mountain, A. et al., "Engineering Antibodies for Therapy," *Biotechnol. Genet. Eng. Rev.*, 1992, 10,1-142.
Orlandi, R., et al., "Cloning immunoglobulin variable domains for expression by the polymerase chain reaction," *Proc. Natl. Acad. Sci. USA*, 1989, 86, 3833-3837.
Riechmann, L., et al., "Reshaping human antibodies for therapy," *Nature*, 1988, 322, 323-327.
Schilizzi, B.M., et al., "Studies on the induction of antigen-specific antibody in anti-CD40 cultured human B lymphocytes," *Developmental Immunology*, 1998, 6, 261-271.
Serotec Product Information Datasheet: "Rabbit anti human interleukin-17," 2002, retrieved from the internet at URL: http://www.serotec.co/asp/datasheet.asp?code=AHP455G, 2 pages.
Takahama H., et al., "Murine IgG1 and IgE memory B cells," 1994, 157(2), 369-380.
Thompson, J., et al., "Affinity maturation of a high-affinity human monoclonal antibody against the third hypervariable loop of human immunodeficiency virus: use of phage display to improve affinity and broaden strain reactivity," *J. of Molecular Biology*, 1996, 256(1), 77-88.
Verma, R., et al., "Antibody engineering: comparison of bacterial, yeast, insect and mammalian expression systems," *J. of Immunological Methods*, 1998, 216, 165-181.
Ward, E.S., et al., "Binding activities of a repertoire of single immunoglobulin variable domains secreted from *Escherichia coli*," *Nature*, 1989, 341, 544-546.
Weitkamp, J.-H., et al., "Generation of recombinant human monoclonal antibodies to rotavirus from single antigen-specific B cells selected with fluorescent virus-like particles," *J. of Immunological Methods*, 2003, 275, 223-237.

* cited by examiner

*Primary Examiner*—David A Saunders
(74) *Attorney, Agent, or Firm*—McDonnell Boehnen Hulbert & Berghoff LLP

(57) ABSTRACT

The invention relates to a method of obtaining an antibody with a desired function, the method comprising: a) bringing a population of B cells into contact with a capturing agent; b) separating the captured B cells from the uncaptured B cells; c) culturing a plurality of captured B cells wherein said B cells have not been sorted into single B cells immediately prior to culturing; d) screening a plurality of the cultured cells to identify cells capable of producing an antibody with the desired function; and e) obtaining the desired antibody therefrom.

9 Claims, 9 Drawing Sheets

METHODS FOR PRODUCING ANTIBODIES

TECHNICAL FIELD

The present invention relates generally to improved methods for producing high affinity antibodies with a desired function. The invention also relates to antibodies produced by the methods of the invention and to antibody producing cells identified and produced in accordance with the methods of the invention.

All documents cited herein are incorporated by reference in their entirety.

BACKGROUND ART

Hybridoma technology for the isolation of monoclonal antibodies is, in general, limited to the generation of rodent mAbs and results in the immortalisation of only a small fraction of the specific antibody-forming cells available in an immunised animal. Antibodies from bacterially expressed libraries are restricted by practical limits to the size of libraries and the requirement for the antibody to be properly folded and expressed in bacteria. In addition, antibodies generated by both these methods frequently require affinity enhancement to obtain antibodies of a high enough affinity for therapeutic use. A number of alternative methods have been designed to enable high affinity antibodies generated during in vivo immune responses to be isolated from any species (Babcook et al., 1996, Proc. Natl. Acad. Sci, 93, 7843-7848; WO 92/02551; de Wildt et al. (1997) Journal of Immunological Methods, 207:61-67 and in Catrin Simonsson Lagerkvist et al. (1995) BioTechniques 18(5):862-869.).

The first alternative method to be designed was the selected lymphocyte antibody method (SLAM) which enables a single lymphocyte that is producing an antibody with a desired specificity to be identified within a large population of lymphoid cells and the genetic information that encodes the specificity of the antibody to be rescued from that lymphocyte. Antibody producing cells which produce antibodies which bind to selected antigens are detected using an adapted haemolytic plaque assay method (Jerne and Nordin, 1963, Science, 140, 405). In this assay, erythrocytes are coated with the selected antigen and incubated with the population of antibody producing cells and a source of complement. Single antibody producing cells are identified by the formation of haemolytic plaques. Plaques of lysed erythrocytes are identified using an inverted microscope and the single antibody producing cell of interest at the centre of the plaque is removed using micromanipulation techniques. The antibody genes from the cell are cloned by reverse transcription PCR. The physical isolation of these cells limits the number of B cells which can be detected and isolated. As a result many of the antibodies isolated may still require affinity enhancement as their affinity may only be in the nanomolar range. See for example, Babcook et al., supra where an affinity of only 1.76 nanomolar ($1.76 \times 10^9$ M$^{-1}$) is described.

In the haemolytic plaque assay described above, the red blood cells are typically coated with antigen via a biotin/streptavidin coupling system that requires the antigen to be biotinylated. This method is therefore restricted to antigens that are available in a pure form and to those that can be biotinylated without affecting epitope presentation. This method clearly precludes the isolation of antibodies against certain types of antigens. For example, many proteins are difficult to purify, particularly cell surface expressed proteins, such as type III proteins. Many proteins alter their conformation and presentation of desirable epitopes upon biotinylation, for example proteins that contain lysine groups in their active site.

It may also be desirable to produce antibodies against unknown antigens, such as proteins expressed on the surface of cells, such as tumour cells and activated T cells. The direct use of tumour cells in the plaque assay instead of antigen coated erythrocytes is difficult to achieve given the requirement for cell lysis to occur in order for plaques containing antibody-producing cells to be identified. Cell lysis is dependent on cell type, antigen and antibody concentration. Red blood cells coated with the desired antigen will bind large amounts of available antibody and will lyse readily in the presence of complement. Other cell types such as tumour cells will not lyse so readily, especially when the availability of antigen on the surface may be very low and hence antibody binding will be low.

In the method of de Wildt et al., B cells from patients suffering from the autoimmune disease systemic lupus erythematosus (in which patients often produce autoantibodies against the U1A protein) were subjected to panning using culture plates coated with U1. Cells which did not bind to the U1A were removed by washing. The adhering cells were then collected from the plates using trypsin treatment and subjected to single cell sorting using a flow cytometer to select individual U1A-specific B cells. Single B cells were then cultured in 96-well plates and clonally expanded. Culture supernatants were then tested for antibody production and U1A-specific B cell clones were identified. Total RNA was then extracted from the positive wells and the $V_H/V_L$ regions from the B cells were cloned.

In Catrin Simonsson Lagerkvist et al. (1995) PBMCs from tetanus-immunized patients which bound tetanus toxoid (TT) were isolated using TT-coated magnetic beads. Single, TT-specific B cells were isolated using an automatic pipette. 0.3 B cells per well were then seeded into 96-well microplates and clonally expanded. The wells were then tested for the presence of TT-specific antibodies. The V-region genes of antibodies from the positive wells were then cloned.

The methods of both de Wildt et al. and Catrin Simonsson Lagerkvist et al. require the isolation of individual B cells which recognise the antigen of interest prior to clonal expansion, which isolation may be both cumbersome and time-consuming. Also, because only one or fewer B cells are seeded in each microtitre well, a large number of microtitre plates is required and must be screened to identify those B cells which specifically recognise the antigen of interest.

Accordingly, there is a need for less labour-intensive methods for isolating antibodies with a desired function. In addition there is a need for higher affinity antibodies which do not require subsequent affinity enhancement.

The present invention provides a method for the isolation of high affinity antibodies with a desired function.

SUMMARY OF THE INVENTION

In accordance with the present invention there is provided a method of obtaining an antibody with a desired function, the method comprising:
  a) bringing a population of B cells into contact with a capturing agent;
  b) separating the captured B cells from the uncaptured B cells;
  c) culturing a plurality of captured B cells wherein said B cells have not been sorted into single B cells immediately prior to culturing;

d) screening a plurality of the cultured cells to identify cells capable of producing an antibody with the desired function; and e) obtaining the desired antibody therefrom.

There are various advantages afforded by the present invention.

For example, the method surprisingly allows the direct isolation of picomolar (or better) antibodies without the need to subsequently affinity mature those antibodies in vitro using methods such as mutagenesis, as is the case for phage and hybridoma derived antibodies. The method of the invention enables the identification of virtually unlimited numbers of unusually high affinity antibodies with a desired function. These high affinity antibodies typically have an affinity in the picomolar range such as those with an affinity of less than 200 pM, less than 100 pM, less than 75 pM, less than 50 pM, less than 25 pM or less than 1 pM. The method of the invention enables one or more of said antibodies to be directly obtained, typically two or more, which to the inventors' belief has not been achieved before.

The method of the invention also enables the identification of antibodies that bind to any antigen, including unknown antigens, cell surface antigens and antigens which cannot be biotinylated, without altering the presentation of desirable epitopes. As a result, antibodies with binding specificities that were previously unattainable by conventional plaque assays can now be produced. In addition, the method of the present invention does not require the isolation of individual antibody-producing cells prior to cloning or that cells are cultured individually in separate unit containers. As a result antibodies can be identified more quickly as the time for plating and screening is reduced compared to various prior art methods.

DETAILED DESCRIPTION OF THE INVENTION

The term "nucleic acid" as used herein includes RNA (e.g. mRNA) and DNA (e.g. cDNA and genomic DNA). The DNA or RNA may be double-stranded or single-stranded. Single-stranded DNA or RNA may be the coding strand, also known as the sense strand, or it may be the non-coding strand, also referred to as the anti-sense strand.

The term 'antibody' as used herein includes any recombinant or naturally occurring immunoglobulin molecule from any antibody class, such as a member of the IgG class e.g. IgG1, IgG2, IgG3 or IgG4 and also any antigen-binding immunoglobulin fragment, such as Fv, Fab, Fab' and F(ab')$_2$ fragments, and any derivatives thereof, such as single chain Fv fragments. Recombinant antibodies can take several different forms and include whole immunoglobulins, chimeric antibodies, humanised antibodies and antigen-binding fragments such as Fv, Fab, Fab' and F(ab')$_2$ fragments, and any derivatives thereof, such as single chain Fv fragments. The methods for creating and manufacturing these antibody molecules are well known in the art (see for example, Boss et al., U.S. Pat. No. 4,816,397; Cabilly et al., U.S. Pat. No. 6,331, 415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585, 089; Adair, WO91/09967; Mountain and Adair, 1992, Biotechnol. Genet. Eng. Rev, 10, 1-142; Verma et al., 1998, Journal of Immunological Methods, 216, 165-181).

The term 'antigen' as used herein refers to any known or unknown substance that can be recognised by an antibody, including proteins, glycoproteins and carbohydrates. Preferably, these antigens include biologically active proteins, such as hormones, cytokines and their cell surface receptors, bacterial or parasitic cell membranes or purified components thereof, and viral antigens.

In one example, the antigen is available in a pure form obtained either by direct purification from the native source or by recombinant expression and purification of said antigen.

In another example, the antigen is one which is difficult to purify. Such antigens include but are not limited to cell surface expressed proteins such as receptors, particularly type III proteins.

In another example, the antigen is one in which the presentation of desirable epitopes on the antigen is altered upon biotinylation. This includes but is not limited to proteins which contain lysines in their active site regions.

In another example, the antigen may be expressed on the surface of a cell, either naturally or recombinantly. Such cells may include but are not limited to mammalian cells, immunomodulatory cells, lymphocytes, monocytes, polymorphs, T cells, tumour cells, yeast cells, bacterial cells, infectious agents, parasites, plant cells, and transfected cells such as NS0, CHO, COS and 293 cells.

In one example, the antigens expressed on the surface of said cells are antigens which are difficult to purify or antigens which lose desired epitopes upon biotinylation such as those antigens described above.

In another example, the antigen is unknown and the antigen is any material that would provide a source of possible antigens. Preferably, that material is of animal, e.g. mammalian, plant, yeast, bacterial or viral origin. The material may be a cell or a population of cells for which it would be desirable to isolate antibodies to, such as mammalian cells, immunomodulatory cells, lymphocytes, monocytes, polymorphs, T cells, tumour cells, yeast cells, bacterial cells, infectious agents, parasites and plant cells. In one embodiment, the cell is a tumour cell.

The term "B cell" as used herein includes any B cell or derivative thereof producing an antibody, such as a B-lymphocyte, a plasma cell, a plasmablast, an activated B cell or a memory B cell. These cells may secrete antibodies and/or maintain antibodies on the surface of the cell.

The population of B cells for use in the present invention will be any population suspected of containing at least one B cell capable of producing antibodies having the desired function.

B cells for use in the invention may be obtained from various sources. For example, B cells can be obtained from an animal which has either been immunized with an antigen, or which has developed an immune response to an antigen as a result of disease. Alternatively, B cells can, for example, be obtained from an immunised naïve animal which has not previously been exposed to the antigen of interest (or an animal which is not known to have been exposed to the antigen of interest or which is not believed to have been exposed to the antigen of interest).

Animals may be immunized with a selected antigen using any of the techniques well known in the art suitable for generating an immune response (see Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized in order to obtain B cells. However, mice, rabbits, pigs and rats are generally preferred.

High numbers of B cells can be found in the peripheral spleen and lymph node of the immunised animal and once an immune response has been generated and the animal has been sacrificed, the spleen and lymph nodes are removed. A single cell suspension of antibody producing cells is prepared using techniques well known in the art.

B cells can also be obtained from an animal that has generated the cells during the course of a disease. For instance, antibody producing cells from a human with a disease of unknown cause, such as cancer, may be obtained and used to assist in the identification of antibodies which have an effect on the disease process or which may lead to identification of an agent or body component that is involved in the cause of the disease. Similarly, B cells may be obtained from subjects with disease of known cause such as malaria or AIDS. These antibody producing cells may be derived from the blood or lymph nodes, as well as from other diseased or normal tissues.

B cells may also be obtained by culture techniques such as in vitro immunization. Examples of such methods are described by C. R. Reading in Methods in Enzymology 121: 18-33 (J. J. Langone, H. H. van Vunakis (eds,), Academic Press Inc., N.Y.).

The method of the present invention employs a capturing agent in step (a). The term "capturing agent" as used herein includes any agent suitable for capturing B cells and is preferably any protein or peptide which will bind to an antibody. Preferably, the capturing agent is an antigen as defined herein before, which is either free in solution or immobilised on a support. Particular supports include plates or beads, e.g. microtitre plates or magnetic beads. Once the B cells and the capturing agent have been in contact for an appropriate time to allow binding the unbound cells may be separated and discarded in part (b) of the process.

By "separating the captured B cells from the uncaptured B cells" we mean separating B cells which bind the capturing agent from those that do not.

Separation may be achieved with the aid of a variety of techniques depending on the nature of the capturing agent such as by panning (see e.g. FIG. 10), using antigen-coated beads (e.g. magnetic beads or streptavidin coated beads), and FACS sorting. Weitkamp et al (2003) *Journal of Immunological Methods* 275, 223-237 describes a FACS sorting method for the isolation of specific B cells.

Preferably, the capturing agent is bound to a solid phase (e.g. a microtitre plate if panning is used or beads if beads are being used) and the B cells are allowed to contact the solid phase for sufficient time to allow binding. B cells which do not bind to the solid phase may then be removed leaving those B cells which are bound to the solid phase. Preferably, the capturing agent is an antigen that is bound to the solid phase in purified form. Alternatively, the capturing agent is a homogeneous or heterogeneous population of cells for which it would be desirable to isolate antibodies to at least some of the surface antigens in the population. Alternatively the capturing agent is a population of transfected cells expressing antigens on their surface.

Thus for example, where the capturing agent is bound to a solid phase panning may be used. In panning, once the antibody producing cells have been in contact with the immobilised capturing agent for sufficient time to allow binding, the mixture is then washed with a medium which facilitates removal of the non-adhering cells from the capturing agent but which leaves cells which bind to the capturing agent adhered to the solid phase via the antibody on the surface of the B cell. Suitable media will be known to those skilled in the art or can be readily determined empirically by those skilled in the art. Any culture medium for example Roswell Park Memorial Institute medium (RPMI) or Dulbecco's Modified Eagle Medium (DMEM) may be used. Preferably, a number of washes is employed to remove the non-adherent cells, e.g. 10 or more washes.

Preferably, panning is conducted using a series of unit containers. By a unit container we refer to containers which are suitable for holding small volumes of liquid, for example a well from a microtitre plate. Preferably, the unit containers each have a similar (e.g ±10%) volume holding capacity and/or inner surface area to a well from a standard 96-well microtitre plate.

Preferably, panning is performed using a microtitre plate. For example 6, 24, 48, 96, 384 or 1536 well microtitre plates may be used. Preferably, the wells in the microtitre plate are each of standard dimensions. Preferably, 96-well microtitre plates having standard-sized wells are used.

Preferably, in the panning step, the capturing agent will saturate the surface of the unit container. Those skilled in the art will be readily able to adjust the parameters of the panning step to optimise the number of B cells which are retained per unit container (e.g. well). Parameters which may be adjusted include the volume or surface area of the unit containers; the concentration or amount of capturing agent bound to the wells; the concentration or amount of B cells administered to the wells; the source of B cells (e.g. if the B cells are from a low responding or naïve individual then more B cells may need to be used); the number of washes to remove the non-adhering cells; and the media used to wash the unit containers.

In an alternative, the capturing agent (e.g. an antigen) may be coated onto beads and beads used to select for those cells which bind to the capturing agent. The use of beads to select for cells which bind to an antigen of interest is well documented in the art. Briefly, for example, the capturing agent is bound to magnetic beads. The B cells are then mixed with the magnetic beads and those B cells which bind to the capturing agent will bind to the magnetic beads via the capturing agent. The B cells which bind to the magnetic beads may then be obtained by magnetic separation.

The use of magnetic beads is described in Catrin Simonsson Lagerkvist et al. (1995) BioTechniques 18(5):862-869. However, contrary to what is taught in Catrin Simonsson Lagerkvist et al., the method of the present invention does not require the isolation of individual B cells (this was achieved in Catrin Simonsson Lagerkvist et al. by directly picking individual magnetic bead-rosetted B cells with an automatic pipette).

Another alternative is FACS sorting, which can be used to select B cells producing the antibody of desired function (see for example Weitkamp et al., (2003) *Journal of Immunological Methods* 275, 223-237). In this technique, the capturing agent (e.g. antigen) may be fluorescently labelled to facilitate the FACS sorting of the B cells which bind to said agent. However, contrary to what is taught in Weitkamp et al., supra the present invention does not require the isolation of individual B cells.

When selecting for those cells which produce an antibody which binds to the antigen of interest, it may be desirable to ensure that B cells which bind non-specifically (e.g. to the solid phase, such as microtitre plates which may be used in panning or to the beads if beads are used or to cells not expressing the antigen) are not selected. In the case of panning this may, for example, be achieved by first exposing the B cells to microtitre plates to which no capturing agent has been bound and then disposing of those B cells which bind non-specifically to the wells. Similarly, if beads are used, then prior to incubating the B cells with capturing agent-coated beads the B cells may first be incubated with uncoated beads and the cells which bind to the uncoated beads may then be removed. Alternatively, cells which bind non-specifically could be removed subsequent to the selection of cells which bind to the capturing agent.

Once the cells which do not bind to the capturing agent are removed, then a plurality of the remaining cells (and in one embodiment all of the remaining cells) are cultured in step (c) without being sorted into single cells immediately prior to culturing. Thus, in contrast to the prior art, the cells which are cultured do not need to have been individually isolated. Indeed, the entirety of the method of the first aspect of the invention may be performed without isolating individual cells which produce antibodies which bind to capturing agent.

Preferably, the separating step is panning and the cultured cells are cultured directly following panning.

Preferably, the cells are cultured in a series of unit containers. Where panning has been used to remove cells which do not bind to the capturing agent, it is preferred that the cells are cultured in the same unit containers in which they were retained by the panning step, in the presence of antigen.

Where cells are retained in the unit containers (e.g. as a result of panning), it is preferred that prior to the removal of cells which do not bind to the capturing agent (in step (a) the number of B cells/well ranges from 100-20,000/well. The number of B cells will depend on the serum titre. For example a serum titre of $1/1,000$-$1/10,000$ would require around 20,000 B cells/well while a titre of $1/100,000$-$1/1,000,000$ would require around 100 B cells/well. Those skilled in the art will be readily able to adjust the parameters of the panning step (e.g. the number and stringency of washes) to optimise the number of B cells which are retained per unit container (e.g. well).

As mentioned above, the B cells are not sorted into single B cells immediately prior to culturing. If a technique such as FACS is used, the B cells are pooled prior to culturing and the unit containers may be seeded with two or more of the B cells. Note that in Catrin Simonsson Lagerkvist et al., 0.3 B cells per well were seeded. In contrast, in the method of the present invention, more than one B cell may be present per unit container.

Where cells are seeded into the unit containers (e.g. as a result of FACS sorting), it is preferred that the unit containers are seeded with between 2 and 100 B cells; more preferably with between 2 and 75 B cells; more preferably between 5 and 50 B cells; more preferably between 5 and 25 B cells; more preferably between 5 and 15 B cells; more preferably between 8 and 12 B cells; yet more preferably about 10 B cells/unit container.

Preferably, the method of the first aspect of the invention does not comprise the isolation of individual cells which produce antibodies having the ability to bind to the antigen of interest, with the optional exception of step b) (e.g. such as where FACS or beads are employed) where individual cells may be isolated before being pooled in step (c).

Preferably, in step c) the B cells are cultured for between 1 day and one month, typically about, or at least, 4, 5, 6, 7, 8, 9 or 10 days or up to one month. Preferably, the B cells are cultured for about 5 to 10 days, more preferably for about 6 to 9, or 6 to 8 days.

Preferably, the cells are cultured under conditions suitable for the clonal expansion of the B cells. Clonal expansion results in a greater quantity of antibody being produced and higher levels of mRNA expression. Clonal expansion is preferably performed in the presence of an antigen to which the antibody with the desired function binds which may assist in the isolation of higher affinity antibodies via in vitro affinity maturation.

Conditions suitable for the clonal expansion of B cells are well known in the art (See for example Catrin Simonsson Lagervist et al., supra). Important conditions include the culture medium, the time for which the cells are cultured, temperature and atmospheric $CO_2$.

Preferably, the B cells are cultured with irradiated EL-4 cells in T cell conditioned media. Preferably, the B cells are cultured with irradiated mutant murine EL-4 thymoma cells, EL-4/B5, in conjunction with human T-cell/macrophage supernatant as a source of proliferation and differentiation factors. The E-4/B5 cells activate the B-cells via a MHC-nonrestricted direct cell-cell interaction. The activation signal itself is not mitogenic but sensitizes the B cells to respond to one (IL-2) or several cytokines present in human T-cell supernatant.

Once the cells have been cultured, a plurality of the cultured cells may be screened in step (d) of the process to ascertain the presence of cells capable of producing an antibody having the desired function. Preferably, this involves screening the culture supernatant of said plurality of cultured cells.

Where cells have been cultured in a series of unit containers, the unit containers can be individually assayed (e.g. by taking culture supernatant from the unit containers) for the presence of cells capable of producing an antibody having the desired function to thereby identify one or more unit containers which are positive for the presence of cells capable of producing an antibody having the desired function. Antibodies with the desired function can then be obtained from a positive unit container. The antibodies can be synthesized directly or indirectly from the cells present in the unit container in step (e) of the method.

It will be appreciated that the present invention may comprise culturing genetically distinct B cells together (i.e. in the same container) whereas in the methods of the prior art antibody-producing cells are individually isolated and then cultured separately (i.e. away from genetically distinct cells).

Surprisingly, it has been found that where a population of genetically distinct B cells are cultured together, usually only nucleic acid encoding one antibody is present/detectable (e.g. by amplification, for instance by PCR) in the culture supernatant of the cultured cells at the end of the culturing period. Accordingly, although a number of B cells may be cultured in the same container in the present invention, it is not generally necessary to identify and isolate one or more B cells from the container which are capable of producing antibodies with the desired function i.e. in general the B cells are clonal.

As mentioned above, in the present invention, there is no need to identify and isolate individual B cells from an individual unit container in which B cells have been cultured. Accordingly, the content of an individual unit container may be screened en bloc. For example, culture supernatant extracted from a series of individual unit containers may each be individually screened allowing for the identification of unit containers which are positive for the presence of cells which produce antibodies having the desired function. Preferably, individual cells which produce antibodies having the desired function are not identified and isolated from the unit containers. Thus in one embodiment of the invention, step d) of the first aspect of the invention does not comprise the isolation of individual cells which produce antibodies with the desired function.

In another embodiment of the invention, steps a) to d) of the first aspect of the invention do not comprise the isolation of individual cells which produce antibodies with the desired function.

The antibodies of the invention may be assayed for a desired function by a variety of methods. The desired function may merely be binding to an antigen of interest or further functional properties may be desired, e.g. high affinity, antagonistic, agonistic or neutralising properties.

Binding to a desired antigen may be assayed for example using immunoassays which include but are not limited to competitive and non-competitive assay systems using techniques such as western blots, radioimmunoassay, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

Preferably, ELISA is used to assay for antibodies which bind to a desired antigen. A typical ELISA protocol comprises preparing antigen, coating the well of a microtitre plate with the antigen, adding the antibody of interest conjugated to a detectable compound, such as an enzyme (e.g., horseradish peroxidase or alkaline phosphatase) to the well and incubating for a period of time and detecting the presence of the antigen. In ELISAs, the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds., (1994), Current Protocols in Molecular Biology, Vol. 1, John Wiley & Sons, Inc., New York, section 1 1.2.1.

Alternatively or in addition, it may be desirable to screen for antibodies which have a desired binding affinity; those recognising a specific epitope; or those antibodies with a functional activity such as neutralising antibodies, antagonistic or agonistic antibodies. Assays for such properties are well known in the art and include, for example, a functional screen of receptor/ligand binding.

Where the method of the invention is carried out using a series of unit containers, it is preferred that culture supernatant from individual unit containers is assayed to identify those containers which are positive for antibodies having the desired function. One or more assays may be performed on the culture supernatant of the unit containers. For instance, it may be desirable to first perform an assay to determine those unit containers positive for antibodies which bind to an antigen of interest. Those unit containers which are positive for antibodies which bind to the antigen of interest may then be screened for the presence of antibodies having a desired affinity or for the presence of antibodies which are neutralising antibodies, antagonistic or agonistic antibodies etc.

The binding affinity of an antibody to an antigen and the off-rate of an antibody-antigen interaction can be determined by BIAcore™ analysis or competitive binding assays. BIAcore™ is an automated biosensor system that can be used to measure molecular interactions (Karlsson, et al., 1991, J. Immunol. Methods, 145, 229-240. One example of a competitive binding assay is a radioimmmoassay comprising the incubation of radio-labelled antigen (e.g., $^3H$ or $^{125}I$) with the antibody of interest in the presence of increasing amounts of unlabelled antigen, and the detection of the antibody bound to the labelled antigen. The affinity of the antibody of interest for a particular antigen and the binding off-rates can be determined from the data by Scatchard plot analysis.

Competition with a second antibody can also be determined using radioimmunoassays. In this case, the antigen is incubated with antibody of interest conjugated to a radiolabel (e.g. $^3H$ or $^{125}I$) in the presence of increasing amounts of an unlabelled second antibody.

Preferably, an assay is performed to identify unit containers which are positive for the presence of high affinity antibodies (antibodies having an affinity in the picomolar range).

The cells which are identified as being capable of producing antibodies with a desired function comprise (and preferably consist of) cells which produce antibodies with a desired function.

Antibodies can be synthesized directly or indirectly from the cells which are capable of producing antibodies with a desired function and which are obtained in step (e) of the process In one embodiment of the invention, step e) of the first aspect of the invention does not comprise the isolation of individual cells which produce antibodies having the desired function.

Preferably, the desired antibody is obtained from a unit container whose content is clonal. The desired antibody may be synthesised directly or indirectly from the cells present in the unit container or from the descendants thereof.

Direct synthesis can be achieved by culturing at least one of the B cells (or a descendant thereof) in an appropriate medium. Preferably, the cells present in a unit container identified as being positive for the presence of cells capable of producing antibodies with a desired function are cultured and the antibody obtained therefrom, optionally by purifying said antibody.

Indirect synthesis can be achieved by isolating the genes encoding the antibody or parts thereof and expressing them (or a modified version thereof) in a host cell. The entire genes may be cloned or the variable regions or portions thereof which confer the desired function of the antibody may be cloned and used to produce recombinant antibodies. Preferably, nucleic acid which encodes the $V_H$ and/or $V_L$ regions or which contains at least one complementarity determining region (CDR) is isolated.

Recombinant antibodies can take several different forms and include whole immunoglobulins, chimeric antibodies, humanised antibodies and antigen binding fragments such as Fv, Fab, Fab' and F(ab')$_2$ fragments, and any derivatives thereof, such as single chain Fv fragments. The methods for creating these antibody molecules are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment, the genes encoding the antibody or parts thereof are amplified from the cultured cells or the descendants thereof. Amplification may be performed directly on the cultured cells or the descendants thereof or there may be a nucleic acid recovery step prior to amplification. Where unit containers are employed, the genes encoding the antibody or parts thereof are amplified from a unit container identified as being positive.

Preferably, amplification is performed using culture supernatant (e.g. in the form of a cell suspension) from a unit container identified as being positive. Again, it is to be emphasised that, contrary to the techniques of the prior art, nucleic acid from unit containers in which a number of genetically distinct cells have been cultured may be amplified.

Through the appropriate selection of primers, the entire sequence encoding the antibody may be amplified or, alternatively, the variable regions or portions thereof which confer the desired function of the antibody may be amplified. Methods for designing primers to amplify all VH and VL gene segments are described in WO92/02551; Babcook et al. supra; Weitkamp et al (2003) *Journal of Immunological Methods* 275, 223-237.

Nucleic acid amplification methods are well known in the art. Where the nucleic acid which has been recovered is RNA, the RNA is preferably reverse transcribed to give cDNA.

Preferably, PCR is used for amplification, preferably RT-PCR. Details of the PCR amplification of antibody-encoding nucleic acid sequences are set forth in WO 92/02551 and are incorporated herein by reference.

In addition to PCR, other amplification procedures may be used. Other amplification procedures include the T7 and Q-replicase methods. The description of these methods in WO 92/02551 is incorporated herein by reference.

Although generally the content of each unit container is clonal, occasionally in some unit containers the content may not be clonal, i.e. more than one antibody is present in the unit container and nucleic acid corresponding to more than one antibody may accordingly be isolated from that unit container. In instances where nucleic acid corresponding to more than one antibody is isolated, it will be necessary to ascertain which of the isolated sequences correspond to antibodies with the desired function. As will be seen from Example 1 below, this may entail testing the various combinations of the amplified $V_H$ and $V_L$ sequences (or portions thereof) to determine those combinations which yield antibodies which are capable of binding to the antigen of interest. Alternatively where nucleic acid corresponding to more than one antibody is isolated from the same unit container there may be occasions where the same sequence is isolated more than once and this dominant sequence may be preferentially tested, as in Example 3. The same sequence may also be found in more than one unit container and this sequence may be preferentially tested as described in Example 3.

Accordingly, the method of the first aspect of the invention may additionally comprise the step that, where nucleic acid corresponding to more than one antibody is amplified, the ability of the amplified nucleic acid to yield antibodies with the desired function is determined. In this way, the amplified nucleic acid which is capable of yielding antibodies with the desired function may be identified and selected.

To some extent, the percentage of "clonal" unit containers is a trade-off between an acceptable number of unit containers which are positive for antibodies with the desired function and an acceptable number of "non-clonal" unit containers. The higher the percentage of positive unit containers present the less likely the content of the containers is to be clonal. The percentage of "clonal" unit containers will depend on a number of factors including the serum titre used and the number of B cells per well. Persons skilled in the art will be able to arrive at an appropriate percentage of "clonal" unit containers by adapting the conditions of the assay as appropriate. Factors which affect the percentage of "clonal" unit containers include the number of B cells present per well before panning.

100-20,000 B cells/well before panning usually results in 1 clone per well. The number of B cells per well prior to panning will depend on the serum titre used as previously described above.

In one embodiment, the genes encoding the antibody or parts thereof are isolated by determining the amino acid sequence of the antibody (or parts thereof) and deducing a nucleic acid sequence therefrom which encodes the antibody or parts thereof. Where unit containers are employed, the sequence of an antibody present in a positive unit container is determined. Because of the degeneracy of the genetic code many different nucleic acid sequences capable of encoding the antibody or portions thereof will exist and therefore a number of suitable nucleic acid sequences may be deduced from the amino acid sequence of the antibody or portions thereof.

As discussed above, in some instances more than one antibody may be produced per unit container. In view of this, in one embodiment the method comprises verifying that the amino acid sequence is from an antibody with the desired function. Alternatively, prior to determining the amino acid sequence, the antibodies present in a unit container may first be purified to ensure that the antibody which is sequenced is an antibody with the desired function.

In one embodiment the genes encoding the antibody or parts thereof are modified prior to expression. Methods of modifying nucleic acids will be well known to those skilled in the art and include, for example, site-directed mutagenesis. Modifications to the nucleic acid may be made at one or more sites. Preferably, the nucleic acid is modified so that a desired function of the encoded amino acid is enhanced, e.g. the resulting antibody has increased binding affinity. Other possible modifications include modifications to increase the stability of the nucleic acid and modifications which confer the encoded polypeptide with additional properties.

The genes encoding the antibody or parts thereof (or modified versions thereof) may be expressed in a host cell to obtain antibody with the desired function.

Suitably, the nucleic acid is incorporated into one or more vectors for expression in a host cell.

Various expression systems available to produce the antibodies of the invention are known in the art and include bacterial, yeast, insect and mammalian expression systems (see for example Verma et al., 1998, Journal of Immunological Methods, 216, 165-181).

As mentioned above, it is preferred that the methods of the invention employ a series of unit containers, preferably wells of a microtitre plate. Accordingly, one embodiment of the invention provides a method of obtaining an antibody with a desired function, the method comprising:

a) bringing a population of B cells into contact with a capturing agent;

b) separating the captured B cells from the uncaptured B cells;

c) culturing a plurality of captured B cells wherein said B cells have not been sorted into single B cells immediately prior to culturing and wherein said B cells are cultured in a series of unit containers;

d) screening the content of at least one unit container to thereby identify at least one unit container positive for the presence of cells capable of producing an antibody with the desired function; and e) obtaining the desired antibody directly or indirectly from a cell in said unit container.

Preferably, the desired antibody is obtained from the unit container by isolating the genes encoding the antibody or parts thereof from a cell present in the unit container, or from a descendant thereof, and expressing the genes encoding the antibody or parts thereof in a suitable host.

In a particularly preferred embodiment of the invention panning is used to obtain an antibody with the desired function. Thus, in a preferred embodiment there is provided a method of obtaining an antibody with a desired function, the method comprising:

a) bringing a population of B cells into contact with a series of unit containers to which a capturing agent is bound;

b) removing from the unit containers those B cells which do not bind to the capturing agent whilst retaining those B cells which do bind to capturing agent;

c) culturing a plurality of the captured B cells in those unit containers in which they are retained, preferably under conditions suitable for clonal expansion;

d) screening the content of at least one unit container to thereby identify at least one unit container positive for the presence of cells capable of producing an antibody with the desired function; and e) obtaining the desired antibody directly or indirectly from said unit container.

A second aspect of the invention provides an antibody obtained by the first aspect of the invention. The antibodies of the present invention may possess various modifications. For example, the antibodies may be conjugated to one or more reporter or effector molecules, for any suitable diagnostic or therapeutic purpose.

The antibody of the invention will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class I antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

Preferably, the antibody obtained by the method of the present invention binds to IL-17. Where it is desired to produce antibodies which recognise IL-17 then the antigen of interest used in the above-described assay will be IL-17, preferably human IL-17.

As mentioned above, the method of the present invention is particularly suited for the identification of high affinity antibodies, typically antibodies having an affinity in the picomolar range, such as those with an affinity of ≦200 pM, 100 pM, 75 pM, 50 pM 25 pM, or 1 pM. In the case of particularly high affinity antibodies it may be more appropriate to describe them in terms of their 'off-rate'. In one embodiment of the invention antibodies are provided with an off rate of less than $1\times10^6$ s$^{-1}$. An antibody is deemed to have an off-rate of less than $1\times10^6$ s$^{-1}$ if its dissociation rate constant is unmeasurable using BIAcore™ analysis.

In a particularly preferred embodiment of the invention there is provided an antibody to IL-17, preferably human IL-17, which has an affinity in the picomolar range. Preferably, the antibody has an affinity of ≦200 pM, 100 pM, 75 pM, 50 pM 25 pM, or 1 pM.

Accordingly, in one embodiment of the first aspect of the invention the method is a method of obtaining an antibody to IL-17 having an affinity in the picomolar range. Preferably, the antibody has an affinity of ≦200 pM, 100 pM, 75 pM, 50 pM 25 pM, or 1 pM.

The antibodies produced by the invention have a number of treatment (both therapeutic and prophylactic), diagnostic and research uses. For example, antibodies to pathogenic microorganisms can be used for treatment of infections by the organisms. Such antibodies can also be used for diagnosis, either in vivo or in vitro. Antibodies directed against cellular receptors can be used to agonize or antagonize receptor function. For example, antibodies directed against adhesion molecules can be used to reduced undesired immune response. Such antibodies can also be used for in vivo imaging of inflammation. Other antibodies may be directed against tumor antigens, and can be used either directly or in combination with an effector molecule for elimination of tumor cells. Antibodies can also be used for diagnosis, either in vitro or in vivo.

A third aspect of the invention provides a panel of high affinity antibodies. The term "panel" is used here to mean a group of two or more (e.g. 2, 3, 4, 5, 8, 10 or more) antibodies which have the same desired function e.g they bind the same antigen. The method according to the present invention allows panels of high affinity antibodies to be simply and directly obtained. It is particularly suited for obtaining panels of antibodies each with an affinity of ≦200 pM, 100 pM, 75 pM, 50 pM 25 pM, 10 pM or 1 pM. Individual antibodies with affinity for a particular antigen as high as this are rare and have been difficult to generate to date. The panel of high affinity antibodies provided by the present invention provides a biased library of antibodies from which useful antibodies may be obtained, for example by further screening.

Further aspects of the invention include:

i) a method of isolating the genes encoding an antibody having a desired function or parts thereof, the method being as described above;

ii) a vector comprising the genes encoding an antibody having a desired function or parts thereof, the method being as described above;

iii) a host cell transformed with the genes encoding an antibody having a desired function or parts thereof, and descendants thereof, the method being as described above; and iv) a method of obtaining an antibody having a desired function, the method comprising culturing a host cell according to iii) and obtaining the antibody produced by the host cell.

EXAMPLES

The present invention will now be described by way of example only.

Example 1

Panning on Solid Phase Purified Mouse Co-Stimulatory Molecule

Rabbits were immunised with four sub-cutaneous injections of a mouse co-stimulatory molecule-rat CD4 fusion protein at three weekly intervals, and peripheral blood B cells were prepared in a mononuclear fraction on Lymphocyte-Rabbit CL-5050 (Cedarlane Laboratories Ltd).

ELISA plates were sterilised with 70% ethanol, washed with sterile PBS three times and air-dried before coating with mouse co-stimulatory molecule-rat CD4 fusion protein at 2 μg/ml overnight at 4° C. Plates were washed in sterile PBS three times, blocked with PBS-10% FCS for one hour, and then washed once in PBS. Cells from the peripheral blood mononuclear fraction from an immunised animal were added at the equivalent of 0.2 ml blood/plate (300 cells/well) and 1 ml blood/plate (1500 cells/well), and allowed to bind for one hour at 37° C. Following extensive washing with media (ten times), during which mononuclear cells and B cells expressing irrelevant antibodies were removed, remaining B cells, expressing specific antibodies, were cultured in the presence of coated antigen, T cell conditioned media (3%) and EL-4 cells ($5 \times 10^4$/well) for seven days.

Figure 1:
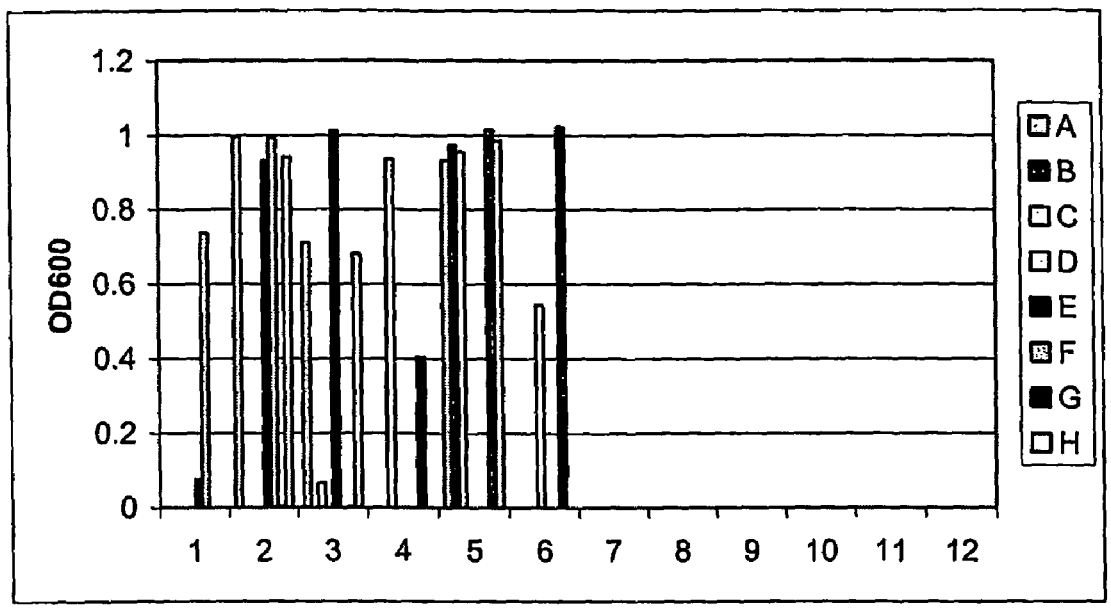
FIG. 1: Binding of antibodies secreted in culture supernatants to solid phase mouse co-stimulatory molecule-rat CD4 fusion protein. Supernatants taken from cultures, where panning had been performed on blocked wells only, failed to bind antigen (columns 7-12). Some 39% of the wells, in which specific enrichment had occurred with B cells from the equivalent of 0.2 ml of blood per plate, contained specific antibody.
Figure 2:
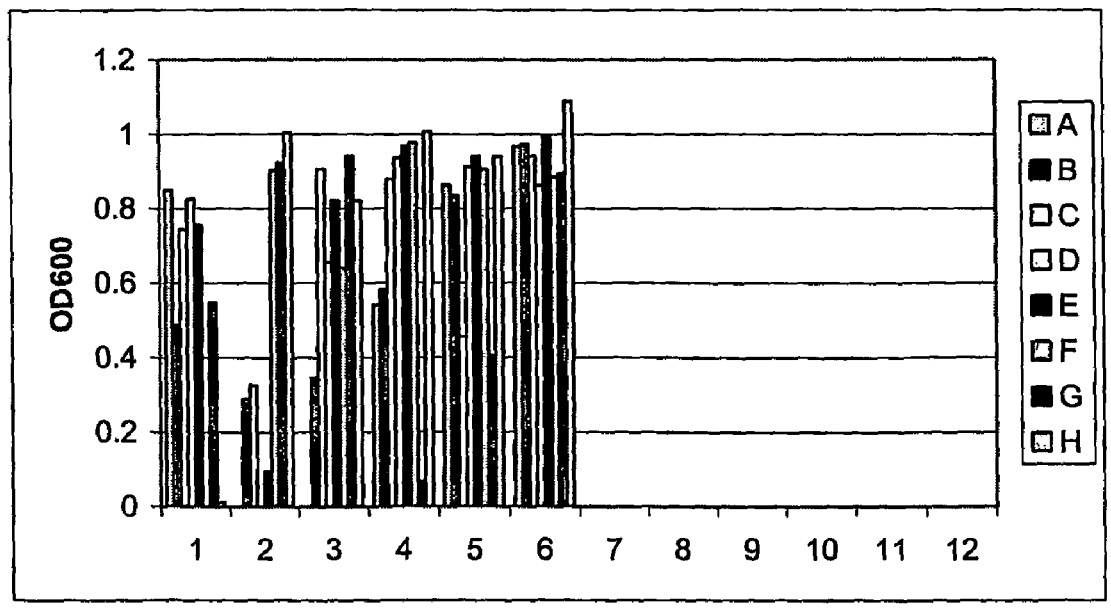
FIG. 2: Binding of antibodies secreted in culture supernatants to solid phase mouse co-stimulatory molecule-rat CD4 fusion protein. Supernatants taken from cultures, where panning had been performed on blocked wells only, failed to bind antigen (columns 7-12). Some 89% of the wells, in which specific enrichment had occurred with B cells from the equivalent of 1 ml of blood per plate, contained specific antibody.

Antibodies secreted in culture supernatants were tested for binding to solid phase mouse co-stimulatory molecule-rat CD4 fusion protein by ELISA, using a goat anti-rabbit Fc-horseradish peroxidase conjugate to reveal the presence of bound antibody by measuring OD at 600 nm. Supernatants taken from cultures, where panning had been performed on blocked wells only, failed to bind antigen (columns 7-12). Some 39% of the wells, in which specific enrichment had occurred with B cells from the equivalent of 0.2 ml of blood per plate, contained specific antibody (FIG. 1), with 89% of the wells positive from the equivalent of 1 ml blood per plate (FIG. 2).

PCR of Wells from Mouse Co-Stimulatory Molecule Solid-Phase Panning

The following wells were selected for further processing: A2, E3, F2 and G6 from the 0.2 ml eqv. blood plate and D6, F4, G3 and H6 from the 11.0 ml eqv. blood plate (numbered 1-8 respectively). Cell culture plates were removed from the −80° C. freezer and wells thawed by gently pipetting up and down with several changes of 100 μl warm media (DMEM or RPMI with 1-6% T cell conditioned medium). The cell suspension was added to a sterile Eppendorf tube and then spun at 2000 rpm for 1 minute in a bench-top centrifuge, rotated 180° and spun again (This helps the formation of a tight pellet). Supernatant was removed and the pellet resuspended in 10 μl of fresh media (DMEM or RPMI with 1-6% T cell conditioned medium). This was then split into 4×2.5 μl aliquots for PCR. A Primary RT-PCR was then performed using the MJ Research RobusT RT-PCR kit (catalogue No. F-580L) using the following mix per tube in order to isolate antibody variable region genes:

|  | μl |
|---|---|
| DEPC water | 35.5 |
| 10× Buffer | 5 |
| dNTPS | 1 |
| 10% NP-40 | 2.5 |
| RNAasin (Promega cat. # N2511) | 0.5 |
| RT | 1 |
| Polymerase | 2 |
| 1° Primer mix (10 μM each primer) | 1 |
| Primers were based on consensus leader and constant region sequences. | |
| MgCl$_2$ | 1.5 |
| Total vol: | 50 |

PCR Program:

| 1. | 50° C. | 30 minutes |
| 2. | 94° C. | 2 minutes |
| 3. | 94° C. | 1 minute |
| 4. | 55° C. | 1 minute |
| 5. | 72° C. | 1 minute |
| 6. | go to step 3 | 40 cycles total |
| 7. | 72° C. | 5 minutes |
| 8. | 4° C. | hold |

1 μl of this reaction was then used to seed separate VH and Vκ secondary PCR reactions using KOD HiFi hot start kit (Novagen, catalogue No. 71086-3) and nested primers containing unique restriction sites to amplify the variable regions. The following mix was prepared per tube:

| | μl |
|---|---|
| Sterile d H₂O | 17.75 |
| 10× KOD PCR buffer | 2.5 |
| KOD HiFi hot start | 0.5 |
| NTPs (2 mM) | 2.5 |
| 2° Primer Mix, Vk or VH (10 uM each primer) | 0.75 |
| MgSO₄ (25 mM) | 1 |
| Total Vol: | 25 |

PCR Programs:

| VH | | Vκ | |
|---|---|---|---|
| 1. 96° C. | 2 minutes | 1. 96° C. | 2 minutes |
| 2. 96° C. | 15 s | 2. 96° C. | 15 s |
| 3. 68° C. | 20 s | 3. 68° C. | 5 s |
| 4. go to step2 | 40 cycles total | 4. go to step 2 | 40 cycles total |
| 5. 4° C. | hold | 5. 4° C. | hold |

Figure 3:
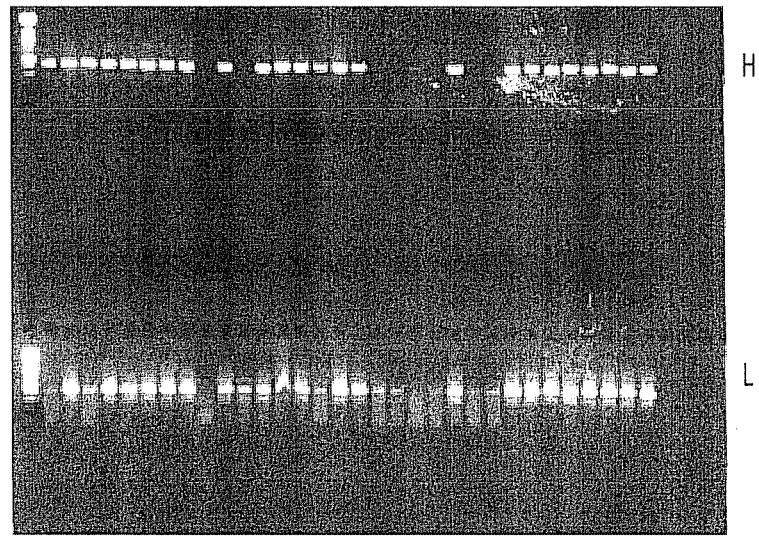
FIG. 3: Agarose gel of 2' PCR products. 4 products for each of the eight selected wells. Sample 1 lanes 1, 3, 5, 7; Sample 2 lanes 9, 11, 13, 15; Sample 3 lanes 2, 4, 6, 8; Sample 4 lanes 10, 12, 14, 16; Sample 5 lanes 17, 19, 21, 23; Sample 6 lanes 25, 27, 29, 31; Sample 7 lanes 18, 20, 22, 24; Sample 8 lanes 26, 28, 30 and 32 VH (top row), Vκ (bottom row).

Following the 2° PCR, fragments were checked by agarose gel electrophoresis (FIG. 3). This gel suggested that PCR products were generated from all 8 wells processed.

Cloning PCR Fragments

PCR fragments were purified using Qiagen Qiaquick 8 PCR purification kit (catalogue No. 28144) and eluted in 60 μl elution buffer. VH fragments were digested with XhoI and HindIII and cloned into the expression vector pMRR14 (mammalian expression construct containing human γ4 CHI, 2 and 3). Vκ fragments were digested with BsiWI and HindIII and cloned into pMRR10.1 (mammalian expression construct containing human Cκ). Both expression vectors are described in WO/03093320. This results in the formation of heavy and light chain rabbit-human chimeric antibody genes. 8×VH and 8×VL clones (plasmid DNA from individual transformed colonies) from each of the 8 wells were sequenced and intra-well alignments performed.

All sequences from wells 1-5, 7 and 8 represented the same antibody variable gene with some minor PCR errors i.e. each of the wells was clonal. Well 6 however exhibited 3 different VH and 3 different VL sequences although there was a dominant sequence in both cases (VH6.1 and Vκ6.1). Consensus sequences were identified and pairs of relevant clones were used for transient expression of rabbit-human chimeric IgGs in CHO cells using the transfection reagent Lipofectamine 2000 (Invitrogen, catalogue No. 11668-019) according to the manufacturers' guidelines. NB There were nine combinations of VH and VL pairs for well 6 (6.1-6.9) (see Table 1).

TABLE 1

VH and Vκ pairs used for transient expression of chimeric IgGs in CHOs.

| Sample id | VH consensus | Vκ consensus |
|---|---|---|
| 1 | VH1 | Vκ1 |
| 2 | VH2 | Vκ2 |
| 3 | VH3 | Vκ3 |
| 4 | VH4 | Vκ4 |
| 5 | VH5 | Vκ5 |
| 7 | VH7 | Vκ7 |
| 8 | VH8 | Vκ8 |
| 6.1 | VH6.1 | Vκ6.1 |
| 6.2 | VH6.1 | Vκ6.2 |
| 6.3 | VH6.1 | Vκ6.3 |
| 6.4 | VH6.2 | Vκ6.1 |
| 6.5 | VH6.2 | Vκ6.2 |
| 6.6 | VH6.2 | Vκ6.3 |
| 6.7 | VH6.3 | Vκ6.1 |
| 6.8 | VH6.3 | Vκ6.2 |
| 6.9 | VH6.3 | Vκ6.3 |

Analysis of Expressed Recombinant IgGs

Following 5 days expression, CHO culture supernatants were harvested and assayed for the presence of IgG and for their ability to bind the mouse co-stimulatory molecule.

For the IgG ELISA, plates were coated with 2 μg/ml anti-human Fc antibody and then blocked in PEG blocker for 1 hour at RT. Plates were washed 3 times before the CHO culture supernatants containing IgG were added to the wells and incubated for 1 hour at RT.

Figure 4:
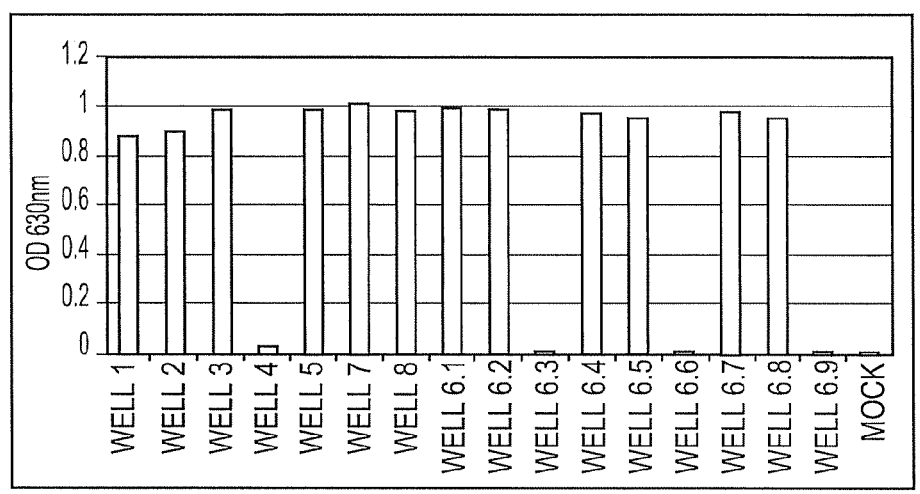
FIG. 4: IgG ELISA of CHO supernatants.

Plates were again washed 3 times and then anti-human F(ab)₂-HRP at 1:5000 dilution in PEG blocker was added to the wells and incubated at RT for 1 hour. Following washing, plates were developed in tetramethyl benzidine (TMB), and Absorbance at 630 nm measured. (See FIG. 4).

For the mouse co-stimulatory molecule ELISA, plates were coated with 2 μg/ml of mouse co-stimulatory molecule and then blocked in PEG blocker for 1 hour at RT. Plates were washed 3 times before the CHO culture supernatants containing IgG were added to the wells and incubated for 1 hour at RT.

Figure 5:
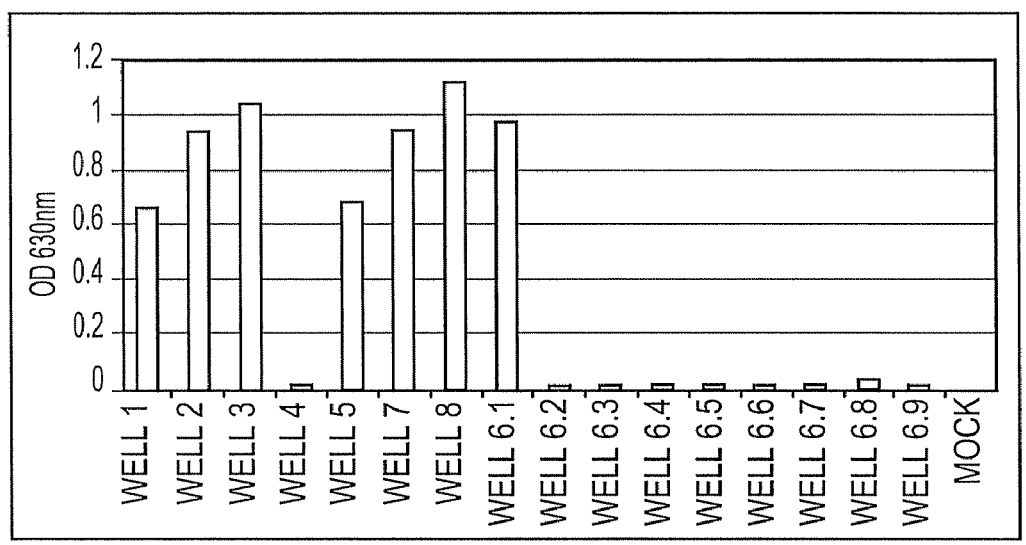
FIG. 5: Mouse co-stimulatory molecule ELISA with CHO supernatants.
Figure 6A:
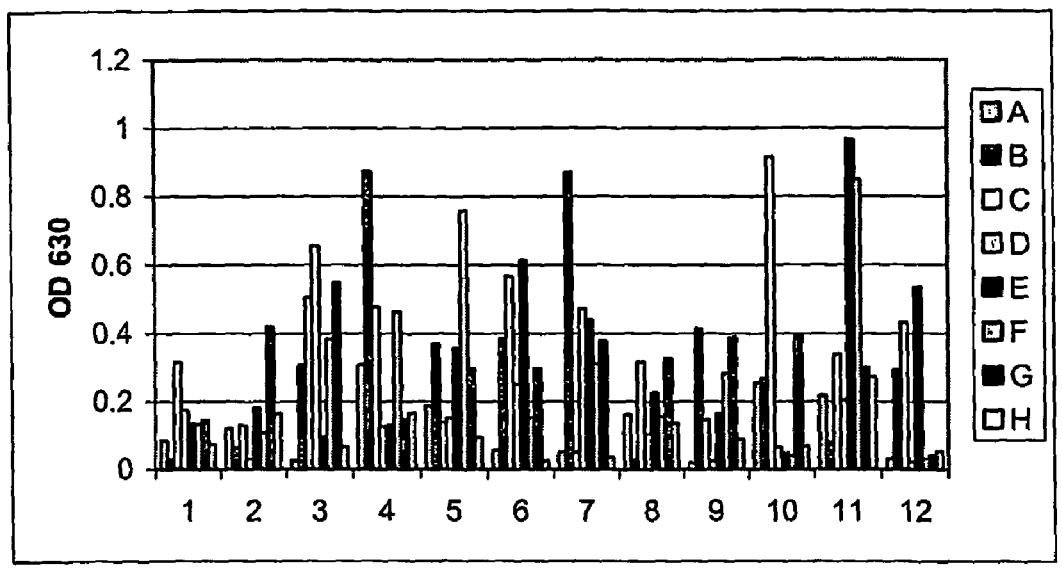
FIG. 6A-D: Binding of antibodies, which had been secreted in culture supernatants, to solid phase human IL-17 protein by ELISA in four microtitre plates (6A-D). The presence of bound rat antibody was revealed with a goat anti-rat Fc polyclonal antibody conjugated to horseradish peroxidase. Supernatants taken from cultures, where panning had been performed on blocked wells only, failed to bind antigen (6D columns 7-12).
Figure 6B:
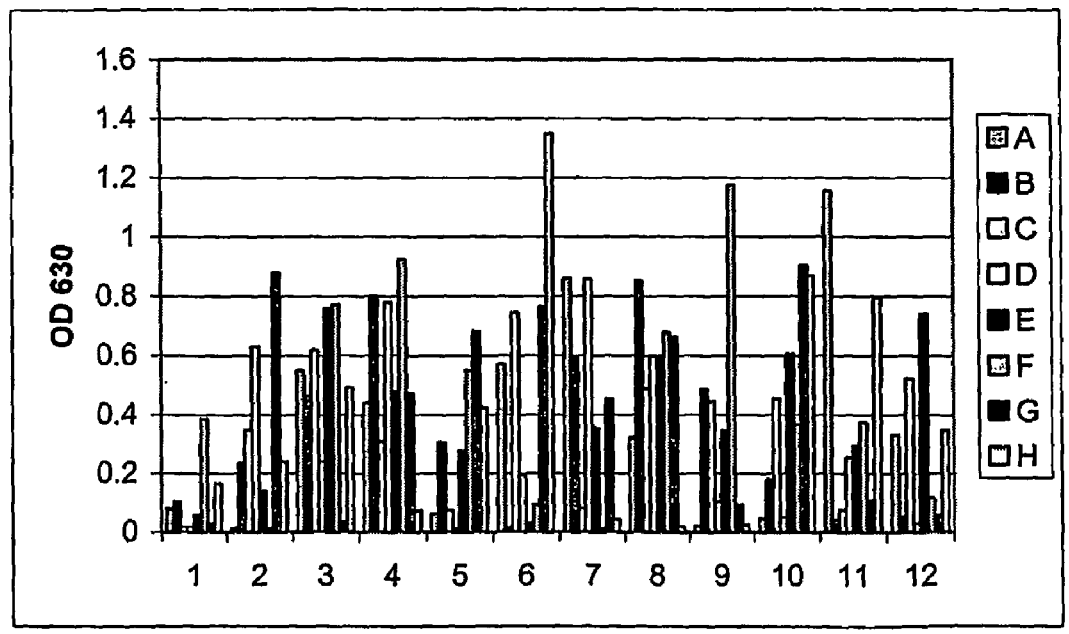
Figure 6C:
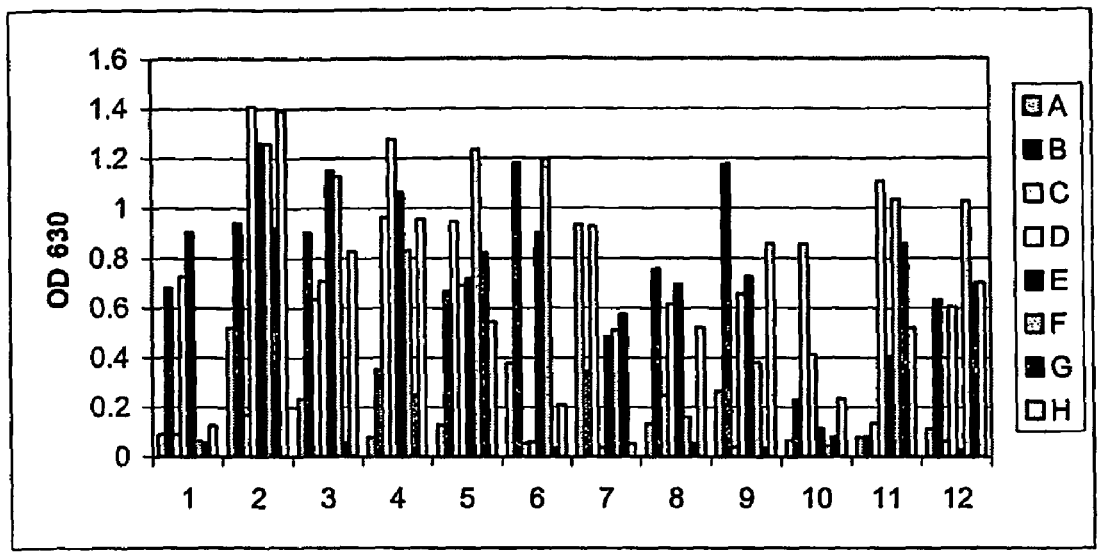
Figure 6D:
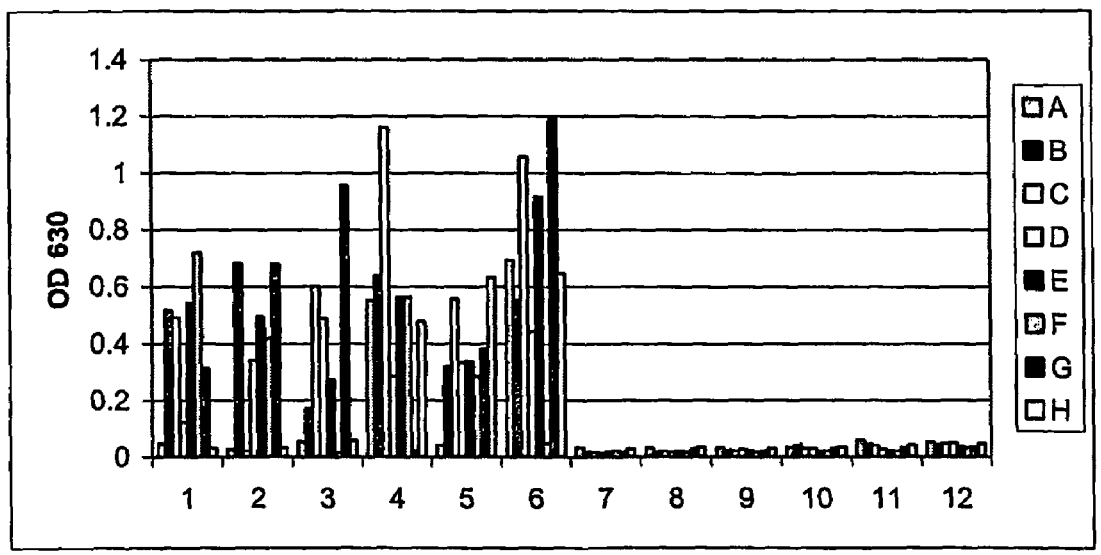

Plates were again washed 3 times and then anti-human Fc-HRP at 1:5000 dilution in PEG blocker was added to the wells and incubated at RT for 1 hour. Following washing plates were developed in TMB and Absorbance at 630 nm measured. (See FIG. 5).

Wells 1, 2, 3, 5, 7 and 8 all produced recombinant chimeric antibody that retained its ability to bind to the mouse co-stimulatory molecule. Well 4 failed to yield any correctly assembled IgG. Out of the 9 possible combinations of IgG (3 VH×3 VL) from well 6, six combinations produced properly assembled antibody. However, only one of these, 6.1, yielded antibody capable of binding to the mouse co-stimulatory molecule. Interestingly this combination represented the antibody that was made up from the VH and Vκ genes that were most dominant in the sequence analysis. In summary, recombinant mouse co-stimulatory molecule-binding antibodies were isolated from 7 out of the 8 wells following panning with B cells on solid phase antigen. Even in the case of well 6, which was not clonal, functional antigen-binding IgG could be recovered.

BIAcore Affinity Measurement of Recombinant IgGs

Recombinant IgG from CHO culture supernatants was captured on a BIAcore™ chip coated with anti-human Fc antibody. The mouse co-stimulatory molecule was then applied to the chip and an affinity determined (Table 2). From the results it is clear that using the method of the present invention it is possible to directly isolate a panel of high affinity antibodies by screening only two microtitre plates.

TABLE 2

Affinity measurement of recombinant IgG from CHO culture supernatants.

| Sample | Conc (ug/mL) | $k_a$ ($M^{-1}s^{-1}$) | $k_d$ ($s^{-1}$) | $K_D$ (pM) |
| --- | --- | --- | --- | --- |
| Well 1 | 0.769 | 1.09e6 | 1.49e−6 | 1.36 |
| Well 2 | 5.450 | 1.04e6 | 4.45e−5 | 43.0 |
| Well 3 | 3.159 | 9.13e5 | 6.82e−6 | 7.46 |
| Well 4 | NIL | | | |
| Well 5 | 3.258 | 1.85e6 | 1.6e−5 | 8.66 |
| Well 6.1 | 4.790 | 6.17e5 | 1.26e−4 | 204 |
| Well 7 | 3.025 | 7.31e5 | 1.25e−6 | 1.71 |
| Well 8 | 3.900 | 2.11e6 | 1.67e−4 | 79.1 |
| Well 6.8 | 2.801 | NB | NB | NB |

NIL = no antibody expression
NB = no binding to mouse co-stimulatory molecule-CD4

Example 2

Panning on Solid Phase Purified Human IL-17

Rats were immunised with four intraperitoneal injections of human IL-17 at three weekly intervals, and single cell suspensions were prepared from spleens.

ELISA plates were sterilised with 70% ethanol, washed with sterile PBS three times and air-dried before coating with human IL-17 protein at 1.25 µg/ml overnight at 4° C. Plates were washed in sterile PBS three times, blocked with PBS-10% FCS for one hour, and then washed once in PBS. Spleen cells from an immunised animal were added to four plates at 50,000 per well, and allowed to bind for one hour at 37° C. Following extensive washing with media (ten times), during which mononuclear cells and B cells expressing irrelevant antibodies were removed, remaining B cells, expressing specific antibodies, were cultured in the presence of coated antigen, T cell conditioned media (3%) and EL-4 cells (5×10⁴/well) for six days. Antibodies, which had been secreted in culture supernatants, were tested for their ability to bind to solid phase human IL-17 protein by ELISA in four microtitre plates (FIGS. 6A-D). The presence of bound rat antibody was revealed with a goat anti-rat Fc polyclonal antibody conjugated to horseradish peroxidase. Supernatants taken from cultures, where panning had been performed on blocked wells only, failed to bind antigen (plate 4 columns 7-12 FIG. 6D). The culture supernatants from Plate 2 (FIG. 6B) were further screened in an in vitro functional assay to measure blocking of IL-17 induced IL-6 release. 60 µl of neat culture supernatant was incubated with 60 µl of hIL-17 (25 ng/ml-1) plus hTNF (2.5 ng/ml-1). These were incubated together for 30 minutes then 100 µl of the mixture was added to 100 µl of cells (3T3-NIH cells, seeded at a density of 0.75×10⁴ cells/well 24 hours before the assay, cells were washed once in fresh media prior to assay). This gives a final dilution factor of 1:4. Plates were incubated for 18 hours (at 37° C.) after which time 100 µl of supernatant was taken and tested for the presence of mIL-6 by ELISA. Concentrations of mIL-6 were ascertained using a standard curve and percentage inhibition of a given well was calculated.

The values shown in Table 3 are percentage inhibition of IL-17 induced IL-6 production in 3T3 fibroblasts. Rows A, G and H were omitted due to lack of culture supernatant. Blockers over or equal to 75% are highlighted on the table.

Plate 2

TABLE 3

| | 2 | 3 | 4 | 5 | 6 | 7 | 8 | 9 | 10 | 11 |
| --- | --- | --- | --- | --- | --- | --- | --- | --- | --- | --- |
| B | 44 | 26 | 73 | 26 | 37 | 38 | ▓ | 53 | 15 | 38 |
| C | 50 | 53 | 37 | 35 | 45 | 44 | 40 | ▓ | 48 | 31 |
| D | ▓ | 45 | 74 | 16 | 45 | ▓ | 71 | 16 | 15 | 30 |
| E | 56 | 70 | ▓ | 34 | 41 | 48 | ▓ | 36 | −27 | 21 |
| F | 42 | ▓ | 68 | 18 | −30 | 68 | ▓ | 61 | 59 | 53 |

The two best wells, C9 and D2 were selected for further analysis and isolation of the variable regions.

Reverse Transcription and PCR Amplification

Complementary DNA was synthesised directly from cells from the two selected wells using Superscript III reverse transcriptase (Invitrogen) and antisense primers specific for $C_H1$, $C_\kappa$ and $C_\lambda$. The reaction mixture was supplemented with 0.5% NP-40 (Calbiochem) and RNasin (Promega) and synthesis performed at 50° C. for 60 min followed by a denaturation step at 70° C. for 15 min.

The cDNAs were then amplified (40 cycles: 94° C., 3 min; 94° C. 30 sec; 50° C. 30 sec; 72° C. 1 min; final extension step 72° C. 5 min) using Stratagene's TaqPlus Precision PCR system, supplemented with 50 µM of each dNTP (Invitrogen), and primers specific for the known variable region families and constant regions of each of the antibody chains. Separate tubes were used for $V_H$, $V_\kappa$ and $V_\lambda$ chain amplifications with each tube containing one tenth of the cDNA generated from the panned lymphocyte cells from each well.

To amplify the PCR products further and to introduce restriction enzyme sites for subsequent cloning, semi-nested PCR was performed. 1 µl from each of the 50 µl primary PCR reactions was transferred into a tube containing equivalent versions of the primary primers but which added suitable restriction enzyme sites. Again the TaqPlus Precision PCR system was used but under modified cycling conditions (40 cycles: 94° C., 3 min; 94° C. 30 sec; 55° C. 30 sec; 72° C. 1 min; final extension step 72° C. 5 min).

PCR products were electrophoresed in 2% agarose gels and bands of the predicted sizes isolated. The fragments were then digested ($V_H$—Hind III-Xho I; $V_\kappa$ and $V_\lambda$—Hind III-Bsi WI), purified and ligated into the corresponding sites within the expression vectors pMRR14 ($V_H$) and pMRR10.1 ($V_\kappa$ and $V_\lambda$).

Figure 7A:
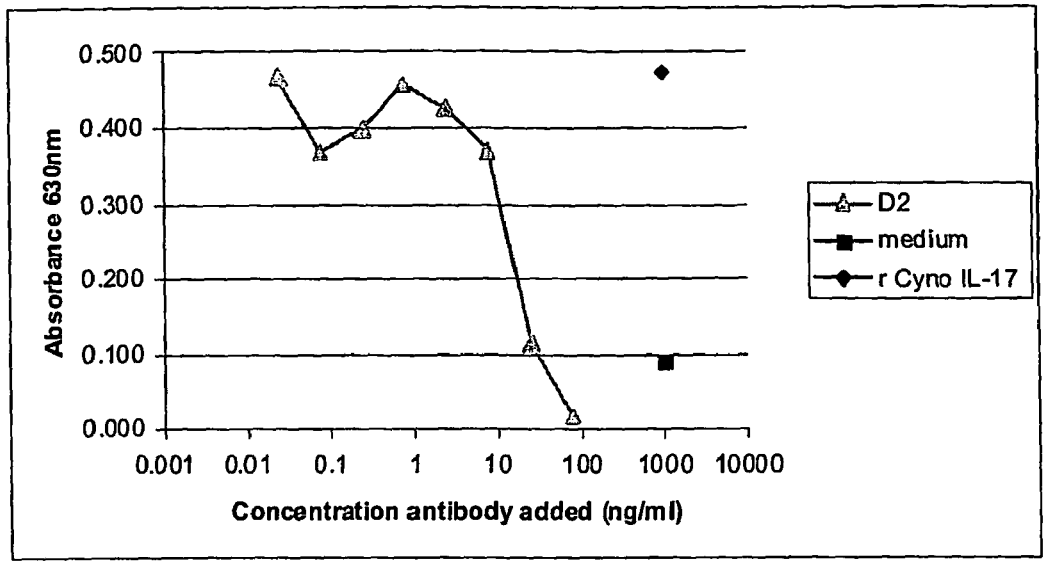
FIG. 7A: Rat anti-human IL-17 antibodies obtained by panning, in a recombinant Cynomologus monkey IL-17 bioassay
Figure 7B:
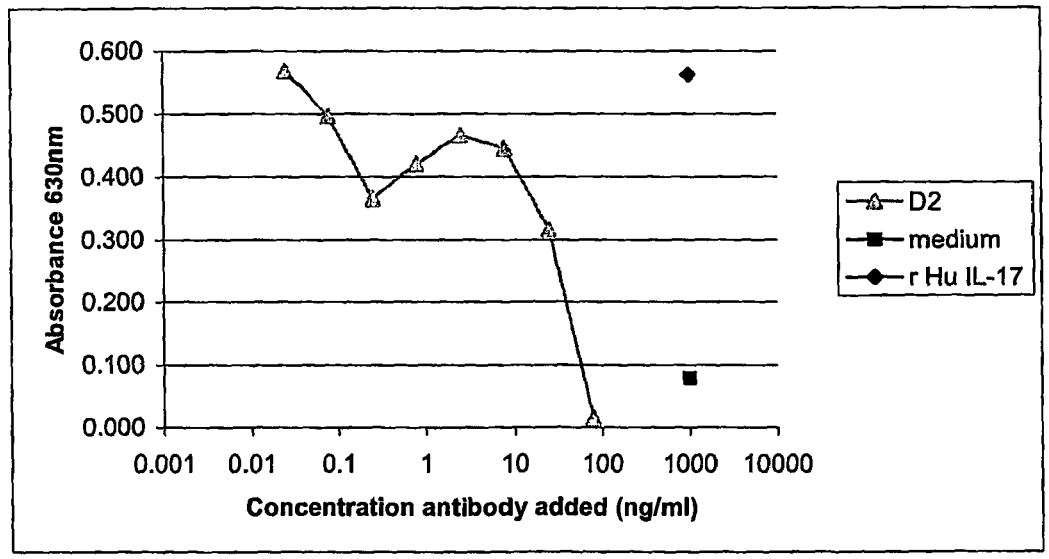
FIG. 7B: Rat anti-human IL-17 antibodies obtained by panning in a recombinant human IL-17 bioassay

Analysis of cloned $V_H$ and $V_\kappa$ indicated that the sequences from both wells were clonal. Transient expression of both clones in CHO cells was performed as described in Example 1. The recombinant antibody from D2 was shown to inhibit the IL-17-mediated production of IL-6 from primary human fibroblasts (FIG. 7).

BIAcore™ Data

Recombinant IgG from CHO culture supernatants was captured on a BIAcore™ chip coated with anti-Fab antibody and IL-17 was passed over in the solution phase and an affinity determined (Table 4). Both clones showed high affinity. This example further demonstrates that a panel of high affinity antibodies can be directly and simply obtained by using the method of the present invention, in this case from a single microtitre plate.

TABLE 4

| Well | $k_a$ | $k_d$ | $K_D$ pM |
|---|---|---|---|
| C9 | 1.8 e6 | 6.3 e−5 | 35 |
| D2 | 2.80 ± 0.01 e6 | 4.23 ± 0.14 e−5 | 15.1 |

Example 3

Panning on Cell-Expressed Antigen

Mouse Co-Stimulatory Molecule

Rabbits were immunised with four sub-cutaneous injections of mouse co-stimulatory molecule-rat CD4 fusion protein at three weekly intervals, and peripheral blood B cells were prepared in a mononuclear fraction on Lymphocyte-Rabbit CL-5050 (Cedarlane Laboratories Ltd).

Figure 8:
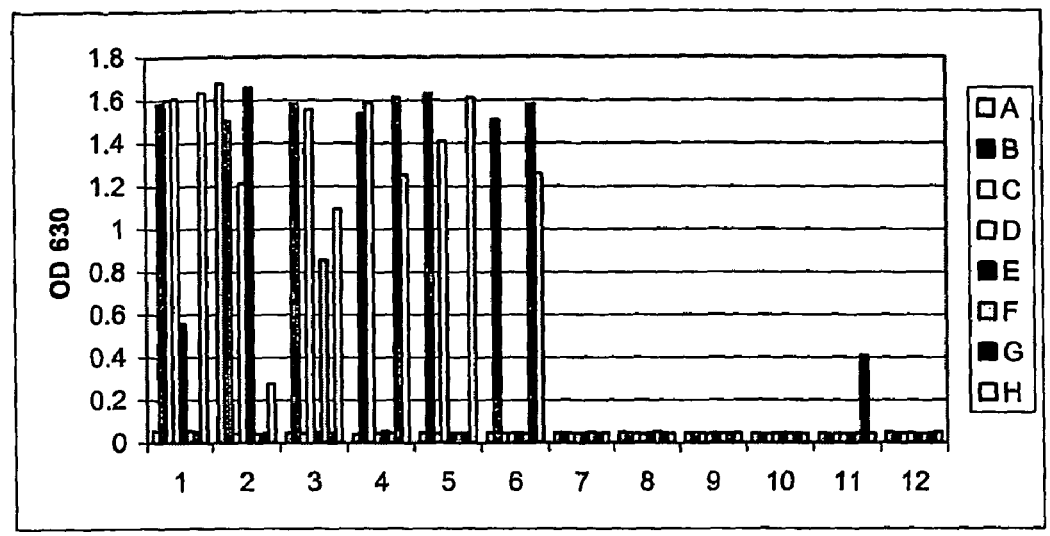
FIG. 8: Binding of antibodies from culture supernatants from a plate to which cells from the equivalent of 3 ml blood had been added to solid phase mouse co-stimulatory molecule-rat CD4 fusion protein by ELISA. Columns 7 to 12 correspond to supernatants from wells where non-transfected CHO cells had been used.
Figure 9:
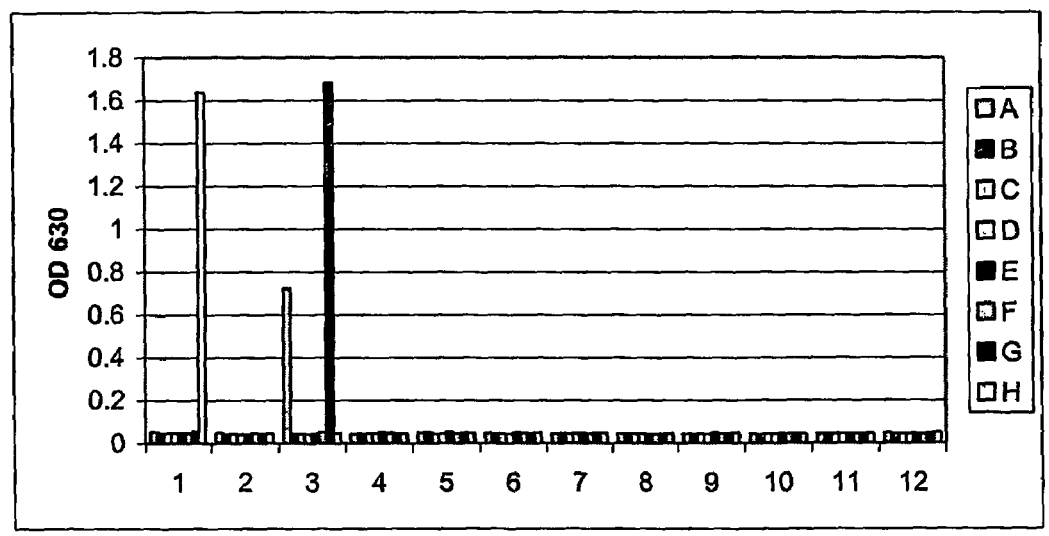
FIG. 9: Binding of antibodies from culture supernatants from a plate to which cells from the equivalent of 0.3 ml blood had been added to solid phase mouse co-stimulatory molecule-rat CD4 fusion protein by ELISA. Columns 7 to 12 correspond to supernatants from wells where non-transfected CHO cells had been used.

The target cells (either parental Chinese Hamster Ovary cells or cells which had been transfected with the gene to express the mouse co-stimulatory molecule) were seeded into wells of a microtitre plate at $3\times10^4$ cells/well and cultured overnight to produce a 70% confluent monolayer. The cells were then fixed with 80% methanol, and the plates blocked with 10% foetal calf serum in PBS. PBMCs from an immunized rabbit were added at the equivalent of 3 ml blood to one plate and 0.3 ml blood equivalent to another and left to bind for 2 hours at 37° C. before extensive washing (10×200 μl/well) to remove mononuclear cells and B cells expressing irrelevant antibodies. After the final wash, 200 μl media as in example 1, with TSN (3%) and EL4.B5 cells ($5\times10^4$/well) were added to the remaining B cells expressing specific antibodies, and the cells were cultured for 7 days. Antibodies secreted in culture supernatants were screened for their ability to bind solid phase, purified antigen-CD4 fusion protein by ELISA. 50% of the wells were positive from the 3 ml blood equivalent plate, and 6% were positive from the 0.3 ml blood equivalent plate (FIGS. 8 and 9). Supernatants taken from cultures, where panning had been performed on untransfected CHO cells, generally failed to bind antigen, with only one exception (Columns 7-12).

Figure 10:
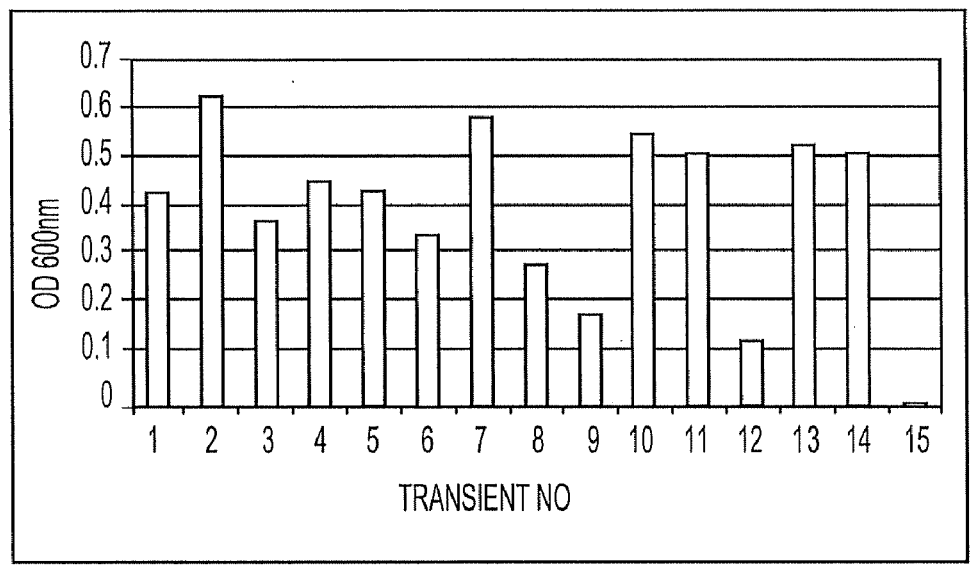
FIG. 10: ELISA analysis of transient expression of clones in CHO cells showing IgG expression.
Figure 11:
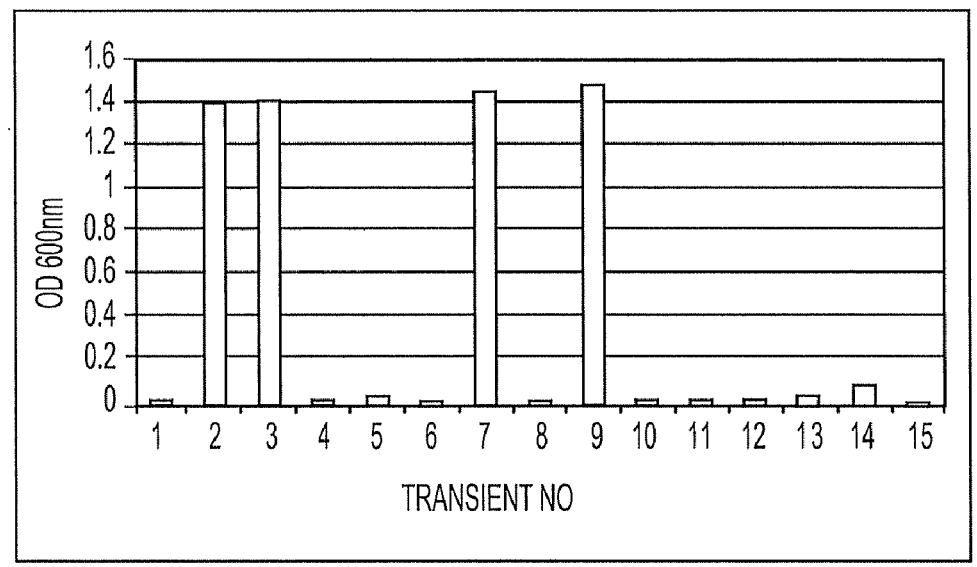
FIG. 11: ELISA analysis of transient expression of clones in CHO cells showing binding to mouse co-stimulatory molecule.
Figure 12:
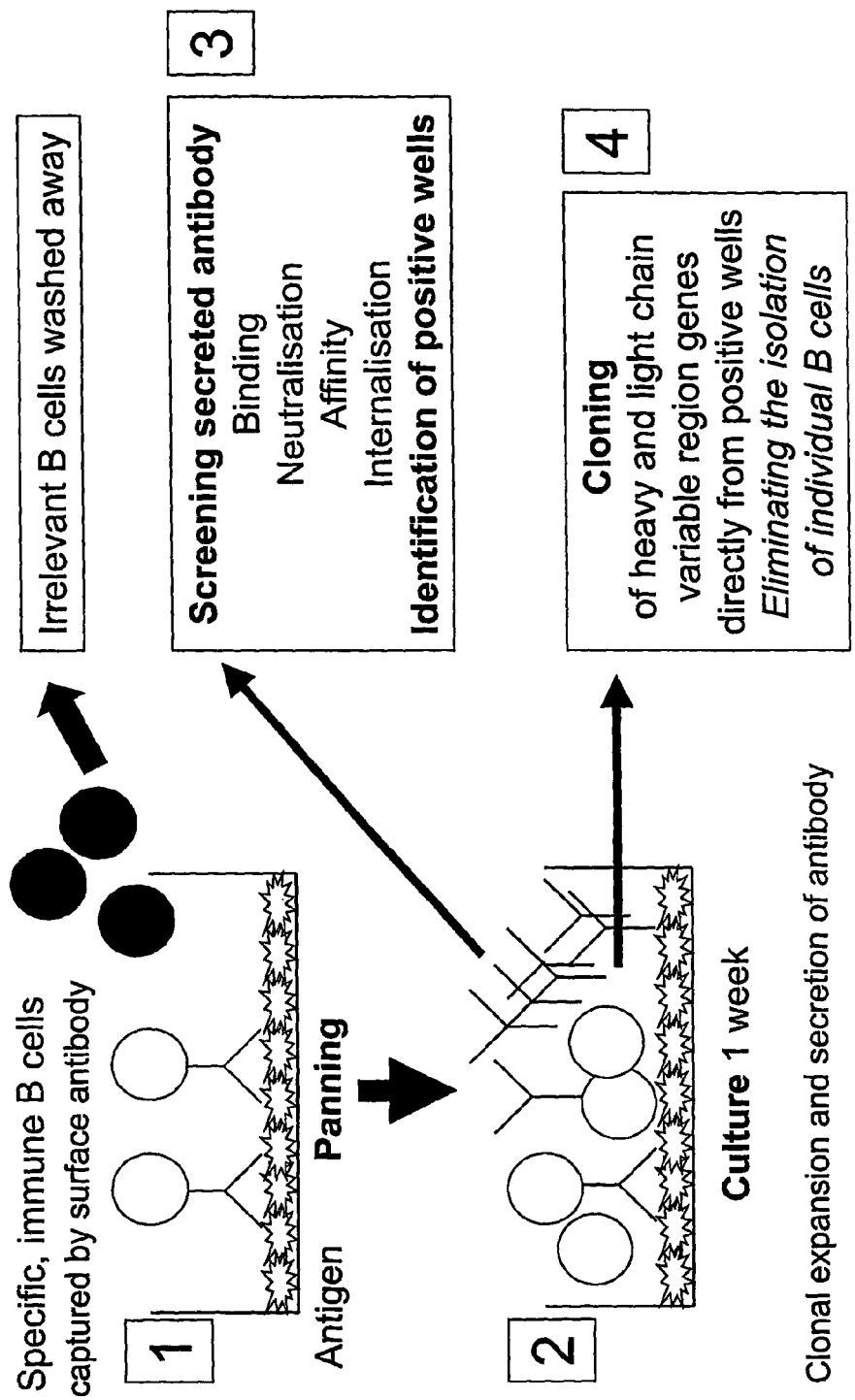
FIG. 12: A panning protocol according to the present invention.

Eight positive wells were selected and PCR performed as described in Example 1 to obtain the antibody variable region sequences. Sequence data from the eight wells showed that clonality had been obtained in one well. In the other wells, in which mixed sequences had been recovered, sequences which represented the dominant sequence in mixtures, and sequences which were identical or very similar from more than one well were taken forward for further study. Transient expression of clones in CHO cells and ELISAs were performed as described in Example 1. IgG expression was confirmed (FIG. 10). Four pairings of heavy and light chains were found to be capable of binding antigen as recombinant products (FIG. 11).

BIAcore™ analysis showed high affinity binding of Clones 3 and 7 to antigen, with unmeasurable dissociation rate constants being recorded, suggesting off-rates less than $1\times10^{-6} s^{-1}$. The affinity ($K_D$) of Clone 2 was determined to be 254 pM, and the affinity of Clone 9 to be 7 nM. This example further demonstrates that a panel of high affinity antibodies can be directly and simply obtained by using the method of the present invention, in this case two of the antibodies having an off rate of less than $1\times10^{-6} s^{-1}$.

It will be understood that the invention has been described by way of example only and modifications may be made whilst remaining within the scope and spirit of the invention.

The invention claimed is:

1. A method of obtaining an antibody that binds an antigen of interest, the method comprising:
    a) bringing a population of B cells into contact with a series of unit containers with an immobilised capturing agent selected from said antigen or a cell expressing on its surface said antigen, whereby at least some of said B cells are captured;
    b) separating the captured B cells of step a) from the uncaptured B cells by removing from the unit containers those B cells which do not bind to the antigen while retaining in a bound state those B cells which do bind to the antigen;
    c) culturing a plurality of the captured B cells in those containers in which they are retained in the presence of the antigen under conditions suitable for clonal expansion of a plurality of captured B cells of step b) wherein said B cells have not been sorted into single B cells immediately prior to culturing;
    d) screening a plurality of the cultured cells of step c) to identify cells capable of producing an antibody that binds to the antigen of interest; and
    e) producing from said identified cells the antibody that binds the antigen of interest, by isolating the genes encoding the antibody that binds the antigen of interest, or the variable regions of the antibody that confer upon the antibody the function of binding the antigen of interest, and expressing the genes or a modified version of the genes in a host cell.

2. A method according to claim 1 wherein step d) comprises assaying at least one unit container for the presence of cells which produce antibodies to the antigen of interest by screening culture supernatant present in the container(s).

3. A method according to claim 2 wherein an assay is performed to identify a unit container which is positive for the presence of cells producing antibodies having affinity equal to or greater than $10^{12}$ liter mol$^{-1}$ to an antigen of interest.

4. A method according to claim 1 wherein in step e) the antibody that binds the antigen of interest is obtained from a unit container whose content is clonal.

5. A method according to claim 1 wherein isolating the genes encoding the antibody or the variable regions of the antibody that confer upon the antibody the function of binding the antigen of interest, comprises amplifying said genes.

6. A method according to claim 5 wherein amplification is performed directly on the cells, or the descendants thereof, which are present in a unit container identified as being positive for the presence of cells which produce antibodies to the antigen of interest.

7. A method according to claim 5 further comprising a nucleic acid recovery step prior to amplification.

8. A method according to claim 1 wherein said genes are modified prior to expression.

9. A method according to claim 1 wherein the capturing agent is IL-17.

* * * * *